(12) United States Patent
Ruelle

(10) Patent No.: US 6,770,459 B1
(45) Date of Patent: Aug. 3, 2004

(54) IMMUNOGENIC COMPOUNDS

(75) Inventor: Jean-Louis Ruelle, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 09/914,168

(22) PCT Filed: Feb. 23, 2000

(86) PCT No.: PCT/EP00/01468

§ 371 (c)(1),
(2), (4) Date: Jan. 28, 2002

(87) PCT Pub. No.: WO00/52042

PCT Pub. Date: Sep. 8, 2000

(30) Foreign Application Priority Data

Feb. 26, 1999 (GB) .............................................. 9904559

(51) Int. Cl.[7] ......................... C12P 21/06; A61K 39/02; C12N 15/09; C12N 1/20

(52) U.S. Cl. .................... 435/69.1; 435/69.3; 435/71.1; 435/320.1; 435/325; 536/23.1; 536/23.7; 530/350; 514/2; 424/251.1; 424/234.1; 424/192.1; 424/190.1

(58) Field of Search ........................... 424/251.1, 234.1, 424/190.1, 185.1, 192.1, 200.1; 435/69.1, 69.7; 536/23.1, 23.4, 24.3

(56) References Cited

FOREIGN PATENT DOCUMENTS

| WO | WO98/28333 | 7/1998 |
|----|------------|--------|
| WO | WO98/06432 | 2/1999 |

*Primary Examiner*—Lynette R. F. Smith
*Assistant Examiner*—Padma Baskar
(74) *Attorney, Agent, or Firm*—Jeffrey A. Sutton; Eric A. Meade

(57) ABSTRACT

The invention provides BASB081 polypeptides and polynucleotides encoding BASB081 polypeptides and methods for producing such polypeptides by recombinant techniques. Also provided are diagnostic, prophylactic and therapeutic uses.

14 Claims, 20 Drawing Sheets

Figure 1A

Identity to SeqID No:1 is indicated by a dot. Gap is indicated by a dash.

```
                  *        20         *
Seqid1 : ATGTCAAAGCCCGTTTTGTTTGCAAATCGC :  30
Seqid3 : ------------------------------ :   -

40         *        60
Seqid1 : AGTTTTATGCCTGTCGCATTGGCGGCTTAT :  60
Seqid3 : ------------------------------ :   -

*        80         *
Seqid1 : TTGCCTTTGATGACATCGCAAGCATTGGCA :  90
Seqid3 : ------------------------------ :   -

100         *       120
Seqid1 : CAACAAAATAACCCTGCAAACATCATCAAT : 120
Seqid3 : .............................. :  30

*       140         *
Seqid1 : CATGTACCCGCTCATGACACCGCCATCAAT : 150
Seqid3 : .............................. :  60

160         *       180
Seqid1 : CAAGCAAAGGCAGGCAATCCGCCTGTTTTG : 180
Seqid3 : .............................. :  90
```

Figure 1B

```
                  *         200              *
Seqid1 : CTAACACCTGAGCAGATACAAGCACGCCTT  :  210
Seqid3 : .............................   :  120

220           *         240
Seqid1 : AATGCTGCTGGACTGAATGCTAAGCCCCAA  :  240
Seqid3 : .............................   :  150

*         260              *
Seqid1 : TCACAAGCTTTGGATGTTGTCAATTTTGAT  :  270
Seqid3 : .............................   :  180

280           *         300
Seqid1 : GATCAATCGCCGATATCTCGTATCGGTGAG  :  300
Seqid3 : .............................   :  210

*         320              *
Seqid1 : CAATCACCCCCTTTGGGTTTGGATATGTCG  :  330
Seqid3 : .............................   :  240

340           *         360
Seqid1 : GTCATCGAAGAAACCACACCGCTAAGCTTG  :  360
Seqid3 : .............................   :  270

*         380              *
Seqid1 : GAGGAATTATTTGCTCAAGAATCTACTGAG  :  390
Seqid3 : .............................   :  300
```

Figure 1C

```
              400           *           420
Seqid1 : ATGGGAATCAATCCAAATGATTATATTCCA :  420
Seqid3 : .............................  :  330

*          440           *
Seqid1 : GAATATCAAGGCGAGCAACCTAATAGTGAG :  450
Seqid3 : .............................  :  360

460           *           480
Seqid1 : GTGGTTGTACCACCGACATTAGAACCTGAA :  480
Seqid3 : .............................  :  390

*          500           *
Seqid1 : AAACCAGGTTTGATCAAGCGTCTTTATGCA :  510
Seqid3 : .............................  :  420

520           *           540
Seqid1 : CGCCTATTTAATGATGGTGTCAATAAGGTG :  540
Seqid3 : .............................  :  450

*          560           *
Seqid1 : CCTAGGCTTAAGGCAAAATTTTATCAATCA :  570
Seqid3 : .............................  :  480

580           *           600
Seqid1 : TCGCAATCAGGCGAAACCAGTGCGATTGGG :  600
Seqid3 : .............................  :  510
```

Figure 1D

```
                *          620            *
Seqid1 : TCATCGCATCAAAAAACAGAGCCTTATGCA : 630
Seqid3 : .............................. : 540

640            *          660
Seqid1 : AATATCAAAGCAGCACTTGAAGACATCACC : 660
Seqid3 : .............................. : 570

*          680            *
Seqid1 : CAAGAGTCAGCGATGGATTTGAATGGCTCT : 690
Seqid3 : .............................. : 600

700            *          720
Seqid1 : ATCCCACGCCTAAGGCAAACTGCTTTGGTG : 720
Seqid3 : .............................. : 630

*          740            *
Seqid1 : GCAGCGCGTGCTGTCGGTTATTATGATATT : 750
Seqid3 : .............................. : 660

760            *          780
Seqid1 : GATTTATCAATCATAAGAAATAGCATCGGA : 780
Seqid3 : .............................. : 690

*          800            *
Seqid1 : GAGGTGGATGTCATCATCCATGATTTAGGT : 810
Seqid3 : .............................. : 720
```

Figure 1E

```
              820              *            840
Seqid1 : GAACCTGTTTATATTGATTATCGAGCGGTG : 840
Seqid3 : ............................. : 750

*             860              *
Seqid1 : GAGGTACGAGGTGAAGGTGCTGATGATAAA : 870
Seqid3 : ............................. : 780

880              *            900
Seqid1 : GCATTTACTACCGTGGCGGATGAGGTGCCA : 900
Seqid3 : ............................. : 810

*             920              *
Seqid1 : TTGCTGATCGGCGATGTCTTTCATCATGGC : 930
Seqid3 : ........................C.... : 840

940              *            960
Seqid1 : AAGTACGAAACCAAAAAAAATCTCATCGAA : 960
Seqid3 : ............................. : 870

*             980              *
Seqid1 : AATGCCAGTGCTGAACATGGATATTTTGAT : 990
Seqid3 : ............................. : 900

1000              *           1020
Seqid1 : GGGCGTTGGCTGGATCGTTCAGTTGATGTA : 1020
Seqid3 : ............................. : 930
```

Figure 1F

```
               *         1040              *
Seqid1 : ATTTTGCCAGATAATACCGCTGATGTCAGC : 1050
Seqid3 : ............................. :  960

1060              *         1080
Seqid1 : TTAATTTATGATACAGGTACGCAGTATCGC : 1080
Seqid3 : ............................. :  990

*         1100              *
Seqid1 : TTTGATGAGGTGGTATTTTTTACCATTGAT : 1110
Seqid3 : ............A................ : 1020

1120              *         1140
Seqid1 : CCTAAAACCAATCAATTGACAACCGATCCA : 1140
Seqid3 : ............................. : 1050

*         1160              *
Seqid1 : GATAAGCTGCCAGTTAAACGAGAATTACTT : 1170
Seqid3 : ............................. : 1080

1180              *         1200
Seqid1 : GAGCAGTTACTCACCGTTAACATGGGAGAG : 1200
Seqid3 : ............................. : 1110

*         1220              *
Seqid1 : GCTTACAATTTACAGGCGGTGCGTGCACTT : 1230
Seqid3 : ............................. : 1140
```

Figure 1G

```
              1240           *           1260
Seqid1 :  TCAAATGATTTGATTGCCACACGGTATTTT  : 1260
Seqid3 :  ..............................  : 1170

*           1280           *
Seqid1 :  AATATGGTGAATACCGAGATTGTCTTTCCA  : 1290
Seqid3 :  ..............................  : 1200

1300           *           1320
Seqid1 :  GAGCGTGAACAGATCCAAAACGACCAAGTG  : 1320
Seqid3 :  ..............................  : 1230

*           1340           *
Seqid1 :  AGCTTTGAGCAGTCTTCAAGTAGCCGTACT  : 1350
Seqid3 :  ..............................  : 1260

1360           *           1380
Seqid1 :  GAACCAGCACAAGTTGATGAAAGCACACTT  : 1380
Seqid3 :  ..............................  : 1290

*           1400           *
Seqid1 :  GAACCTGTCATTGAAACCGTTGAGCTAACG  : 1410
Seqid3 :  ..............................  : 1320

1420           *           1440
Seqid1 :  GATGGGATATTAATGGATATTTCGCCCATC  : 1440
Seqid3 :  ..............................  : 1350
```

Figure 1H

```
                           *         1460              *
Seqid1 : GAATTTAGTGCATCTAATCTGATTCAAGAC : 1470
Seqid3 : ............................. : 1380

1480              *         1500
Seqid1 : AAGCTAAATTTGGTGGCTGCCAAGGCTCGC : 1500
Seqid3 : ............................. : 1410

*         1520              *
Seqid1 : CATTTATATGACATGCCTGATGATAGGGTG : 1530
Seqid3 : ............................. : 1440

1540              *         1560
Seqid1 : CTTGCCATCAATCATGATGATGGCGTAAAT : 1560
Seqid3 : ............................. : 1470

*         1580              *
Seqid1 : CGCTCTATTTTGGGCAGAATCAGCGATGCC : 1590
Seqid3 : ............................. : 1500

1600              *         1620
Seqid1 : GTATCTGCCGTTGCACGTGCTATTTTACCT : 1620
Seqid3 : ............................. : 1530

*         1640              *
Seqid1 : GATGAATCTGAAAATGAGGTAATAGATTTG : 1650
Seqid3 : ............................. : 1560
```

Figure 1I

```
              1660            *          1680
Seqid1 : CCCGAGCGTACCGCATTGGCTAATCGCAAG : 1680
Seqid3 : ............................. : 1590

*          1700            *
Seqid1 : ACCCCTGCTGATGTCTATCAAAGTAAAAAA : 1710
Seqid3 : ............................. : 1620

1720            *          1740
Seqid1 : GTGCCGCTATATGTCTTTGTGGCGAGTGAT : 1740
Seqid3 : ............................. : 1650

*          1760            *
Seqid1 : AAACCACGAGATGGTCAAATTGGTTTGGGC : 1770
Seqid3 : .....C....................... : 1680

1780            *          1800
Seqid1 : TGGGGATCGGACACAGGTACCCGCCTAGTC : 1800
Seqid3 : ............................. : 1710

*          1820            *
Seqid1 : ACAAAATTTGAGCATAATTTGATTAATCGT : 1830
Seqid3 : ............................. : 1740

1840            *          1860
Seqid1 : GATGGCTATCAAGCAGGCGCTGAGCTAAGA : 1860
Seqid3 : ............................. : 1770
```

Figure 1J

```
             *         1880              *
Seqid1 : CTGTCTGAGGATAAAAAGGGGTCAAGTTA : 1890
Seqid3 : ............................ : 1800

1900             *         1920
Seqid1 : TATGCCACCAAACCGCTTAGCCACCCTCTA : 1920
Seqid3 : ............................ : 1830

*         1940              *
Seqid1 : AATGATCAGCTAAGAGCAACTTTGGGTTAT : 1950
Seqid3 : ............................ : 1860

1960             *         1980
Seqid1 : CAACAAGAAGTTTTTGGTCACTCTACCAAT : 1980
Seqid3 : ............................ : 1890

*         2000              *
Seqid1 : GGTTTTGATTTATCCACACGCACCCTAGAG : 2010
Seqid3 : ............................ : 1920

2020             *         2040
Seqid1 : CATGAGATTAGCCGCAGTATTATCCAAAAT : 2040
Seqid3 : ............................ : 1950

*         2060              *
Seqid1 : GGTGGCTGGAATCGTACTTATTCATTGCGT : 2070
Seqid3 : ............................ : 1980
```

Figure 1K

```
              2080           *          2100
Seqid1 : TATCGTCTTGATAAGCTTAAAACCCAAGCA : 2100
Seqid3 : ............................. : 2010

*           2120           *
Seqid1 : CCCCCTGAAACATGGCAGGATTTACCAGTG : 2130
Seqid3 : ............................. : 2040

2140           *          2160
Seqid1 : GATTTTGTCAATGGTAAGCCAAGCCAAGAG : 2160
Seqid3 : ............................. : 2070

*           2180           *
Seqid1 : GCGTTATTGGCAGGTGTTGCTGTGCATAAA : 2190
Seqid3 : ............................. : 2100

2200           *          2220
Seqid1 : ACGGTTGCAGATAATTTGGTTAATCCGATG : 2220
Seqid3 : ............................. : 2130

*           2240           *
Seqid1 : CGTGGCTATCGTCAGCGATATTCTTTAGAG : 2250
Seqid3 : ............................. : 2160

2260           *          2280
Seqid1 : GTTGGCTCAAGCGGTTTGGTATCGGATGCT : 2280
Seqid3 : ............................. : 2190
```

Figure 1L

```
                  *         2300            *
Seqid1 : AATATGGCTATTGCTCGAGCTGGTATTAGT : 2310
Seqid3 : ............................. : 2220

2320           *          2340
Seqid1 : GGCGTGTATAGTTTTGGGGATAATGCTTAT : 2340
Seqid3 : ............................. : 2250

*         2360            *
Seqid1 : GGCAGCAATCGTGCCCATCAGATGACTGGT : 2370
Seqid3 : ............................. : 2280

2380           *          2400
Seqid1 : GGCATACAAGCAGGATACATTTGGTCGGAT : 2400
Seqid3 : ............................. : 2310

*         2420            *
Seqid1 : AATTTTAATCATGTGCCATATCGTTTGCGT : 2430
Seqid3 : ............................. : 2340

2440           *          2460
Seqid1 : TTTTTTGCTGGTGGCGACCAAAGTATTCGT : 2460
Seqid3 : ............................. : 2370

*         2480            *
Seqid1 : GGATATGCACATGACAGTTTATCACCTATA : 2490
Seqid3 : ............................. : 2400
```

Figure 1M

```
                  2500           *         2520
Seqid1 : TCAGATAAGGGTTATCTGACAGGCGGTCAA : 2520
Seqid3 : .............................. : 2430

*         2540           *
Seqid1 : GTATTGGCGGTTGGTACAGCTGAATATAAT : 2550
Seqid3 : .............................. : 2460

2560           *         2580
Seqid1 : TATGAATTTATGAAAGATTTGCGTTTGGCG : 2580
Seqid3 : .............................. : 2490

*         2600           *
Seqid1 : GTTTTTGGTGATATTGGTAATGCTTATGAT : 2610
Seqid3 : .............................. : 2520

2620           *         2640
Seqid1 : AAAGGCTTTACTAATGATACCAAAATTGGT : 2640
Seqid3 : .............................. : 2550

*         2660           *
Seqid1 : GCAGGTGTCGGTGTTCGCTGGGCATCACCT : 2670
Seqid3 : .............................. : 2580

2680           *         2700
Seqid1 : GTCGGTCAAGTTCGTGTTGATGTGGCAACT : 2700
Seqid3 : .............................. : 2610
```

Figure 1N

```
                  *         2720              *
Seqid1 : GGTGTCAAAGAAGAGGGCAATCCCATTAAG : 2730
Seqid3 : ............................. : 2640

2740              *       2760
Seqid1 : CTGCATTTTTTTATTGGCACACCATTTTAA : 2760
Seqid3 : .............................. : 2670
```

Figure 2A

Identity to SeqID No:2 is indicated by a dot. Gap is indicated by a dash.

```
                    *         20          *
Seqid2 : MSKPVLFANRSFMPVALAAYLPLMTSQALA :  30
Seqid4 : ------------------------------ :   -

40          *          60
Seqid2 : QQNNPANIINHVPAHDTAINQAKAGNPPVL :  60
Seqid4 : .............................. :  30

*         80          *
Seqid2 : LTPEQIQARLNAAGLNAKPQSQALDVVNFD :  90
Seqid4 : .............................. :  60

100         *         120
Seqid2 : DQSPISRIGEQSPPLGLDMSVIEETTPLSL : 120
Seqid4 : .............................. :  90

*        140          *
Seqid2 : EELFAQESTEMGINPNDYIPEYQGEQPNSE : 150
Seqid4 : .............................. : 120

160         *         180
Seqid2 : VVVPPTLEPEKPGLIKRLYARLFNDGVNKV : 180
Seqid4 : .............................. : 150
```

Figure 2B

```
                       *         200              *
Seqid2 :  PRLKAKFYQSSQSGETSAIGSSHQKTEPYA  : 210
Seqid4 :  ..............................  : 180

220              *         240
Seqid2 :  NIKAALEDITQESAMDLNGSIPRLRQTALV  : 240
Seqid4 :  ..............................  : 210

*         260              *
Seqid2 :  AARAVGYYDIDLSIIRNSIGEVDVIIHDLG  : 270
Seqid4 :  ..............................  : 240

280              *         300
Seqid2 :  EPVYIDYRAVEVRGEGADDKAFTTVADEVP  : 300
Seqid4 :  ..............................  : 270

*         320              *
Seqid2 :  LLIGDVFHHGKYETKKNLIENASAEHGYFD  : 330
Seqid4 :  ..............................  : 300

340              *         360
Seqid2 :  GRWLDRSVDVILPDNTADVSLIYDTGTQYR  : 360
Seqid4 :  ..............................  : 330

*         380              *
Seqid2 :  FDEVVFFTIDPKTNQLTTDPDKLPVKRELL  : 390
Seqid4 :  ..............................  : 360
```

Figure 2C

```
                400           *           420
Seqid2  :  EQLLTVNMGEAYNLQAVRALSNDLIATRYF  :  420
Seqid4  :  .............................   :  390

*           440           *
Seqid2  :  NMVNTEIVFPEREQIQNDQVSFEQSSSSRT  :  450
Seqid4  :  .............................   :  420

460           *           480
Seqid2  :  EPAQVDESTLEPVIETVELTDGILMDISPI  :  480
Seqid4  :  .............................   :  450

*           500           *
Seqid2  :  EFSASNLIQDKLNLVAAKARHLYDMPDDRV  :  510
Seqid4  :  .............................   :  480

520           *           540
Seqid2  :  LAINHDDGVNRSILGRISDAVSAVARAILP  :  540
Seqid4  :  .............................   :  510

*           560           *
Seqid2  :  DESENEVIDLPERTALANRKTPADVYQSKK  :  570
Seqid4  :  .............................   :  540

580           *           600
Seqid2  :  VPLYVFVASDKPRDGQIGLGWGSDTGTRLV  :  600
Seqid4  :  .............................   :  570
```

Figure 2D

```
                    *          620            *
Seqid2 :  TKFEHNLINRDGYQAGAELRLSEDKKGVKL  : 630
Seqid4 :  ............................    : 600

640            *           660
Seqid2 :  YATKPLSHPLNDQLRATLGYQQEVFGHSTN  : 660
Seqid4 :  ............................    : 630

*          680            *
Seqid2 :  GFDLSTRTLEHEISRSIIQNGGWNRTYSLR  : 690
Seqid4 :  ............................    : 660

700            *           720
Seqid2 :  YRLDKLKTQAPPETWQDLPVDFVNGKPSQE  : 720
Seqid4 :  ............................    : 690

*          740            *
Seqid2 :  ALLAGVAVHKTVADNLVNPMRGYRQRYSLE  : 750
Seqid4 :  ............................    : 720

760            *           780
Seqid2 :  VGSSGLVSDANMAIARAGISGVYSFGDNAY  : 780
Seqid4 :  ............................    : 750

*          800            *
Seqid2 :  GSNRAHQMTGGIQAGYIWSDNFNHVPYRLR  : 810
Seqid4 :  ............................    : 780
```

Figure 2E

```
              820           *          840
Seqid2 : FFAGGDQSIRGYAHDSLSPISDKGYLTGGQ : 840
Seqid4 : .............................. : 810

*           860           *
Seqid2 : VLAVGTAEYNYEFMKDLRLAVFGDIGNAYD : 870
Seqid4 : .............................. : 840

880           *          900
Seqid2 : KGFTNDTKIGAGVGVRWASPVGQVRVDVAT : 900
Seqid4 : .............................. : 870

*     919
Seqid2 : GVKEEGNPIKLHFFIGTPF : 919
Seqid4 : ..................F : 889
```

IMMUNOGENIC COMPOUNDS

FIELD OF THE INVENTION

This invention relates to polynucleotides, (herein referred to as "BASB081 polynucleotide(s)"), polypeptides encoded by them (referred to herein as "BASB081" or "BASB081 polypeptide(s)"), recombinant materials and methods for their production. In another aspect, the invention relates to methods for using such polypeptides and polynucleotides, including vaccines against bacterial infections. In a further aspect, the invention relates to diagnostic assays for detecting infection of certain pathogens

BACKGROUND OF THE INVENTION

*Moraxella catarrhalis* (also named *Branhamella catarrhalis*) is a Gram negative bacteria frequently isolated from the human upper respiratory tract. It is responsible for several pathologies the main ones being otitis media in infants and children, and pneumonia in elderlies. It is also responsible of sinusitis, nosocomial infections and less frequently of invasive diseases.

Otitis media is an important childhood disease both by the number of cases and its potential sequelae. More than 3.5 millions cases are recorded every year in the United States, and it is estimated that 80% of the children have experienced at least one episode of otitis before reaching the age of 3 (Klein, J O (1994) Clin.Inf.Dis 19:823). Left untreated, or becoming chronic, this disease may lead to hearing losses that could be temporary (in the case of fluid accumulation in the middle ear) or permanent (if the auditive nerve is damaged). In infants, such hearing losses may be responsible for a delayed speech learning.

Three bacterial species are primarily isolated from the middle ear of children with otitis media: *Streptococcus pneumoniae*, non typeable *Haemophilus influenza* (NTHi) and *M. catarrhalis*. They are present in 60 to 90% of the cases. A review of recent studies shows that *S. pneumoniae* and NTHi represent both about 30%, and *M. catarrhalis* about 15% of the otitis media cases (Murphy, T F (1996) Microbiol.Rev. 60:267). Other bacteria could be isolated from the middle ear (*H. influenza* type B, *S. pyogenes* etc) but at a much lower frequency (2% of the cases or less).

Epidemiological data indicate that, for the pathogens found in the middle ear, the colonization of the upper respiratory tract is an absolute prerequisite for the development of an otitis; other are however also required to lead to the disease (Dickinson, D P et al. (1988) J. Infect.Dis. 158:205, Faden, H L et al. (1991) Ann.Otorhinol.Laryngol. 100:612). These are important to trigger the migration of the bacteria into the middle ear via the Eustachian tubes, followed by the initiation of an inflammatory process. These factors are unknown todate. It has been postulated that a transient anomaly of the immune system following a viral infection, for example, could cause an inability to control the colonization of the respiratory tract (Faden, H L et al. (1994) J. Infect.Dis. 169:1312). An alternative explanation is that the exposure to environmental factors allow a more important colonization of some children, who subsequently become susceptible to the development of otitis media because of the sustained presence of middle ear pathogens (Murphy, T F (1996) Microbiol.Rev. 60:267).

The immune response to *M. catarrhalis* is poorly characterized. The analysis of strains isolated sequentially from the nasopharynx of babies followed from 0 to 2 years of age, indicates that they get and eliminate frequently new strains. This indicates that an efficacious immune response against this bacteria is mounted by the colonized children (Faden, H L et al. (1994) J. Infect.Dis. 169:1312).

In most adults tested, bactericidal antibodies have been identified (Chapman, A J et al. (1985) J. Infect.Dis. 151:878). Strains of *M. catarrhalis* present variations in their capacity to resist serum bactericidal activity, in general, isolates from diseased individuals are more resistant than those who are simply colonized (Hol, C et al. (1993) Lancet 341:1281, Jordan, K L et al. (1990) Am.J.Med. 88 (suppl. 5A):28S). Serum resistance could therfore be considered as a virulence factor of the bacteria. An opsonizing activity has been observed in the sera of children recovering from otitis media.

The antigens targetted by these different immune responses in humans have not been identified, with the exception of OMP B1, a 84 kDa protein which expression is regulated by iron, and that is recognized by the sera of patients with pneumonia (Sethi, S, et al. (1995) Infect.Immun. 63:1516), and of UspA1 and UspA2 (Chen D. et al.(1999), Infect.Immun. 67:1310).

A few other membrane proteins present on the surface of *M. catarrhalis* have been characterized using biochemical method, or for their potential implication in the induction of a protective immunity (for review, see Murphy, T F (1996) Microbiol.Rev. 60:267). In a mouse pneumonia model, the presence of antibodies raised against some of them (UspA, CopB) favors a faster clearance of the pulmonary infection. Another polypeptide (OMP CD) is highly conserved among *M. catarrhalis* strains, and presents homologies with a porin of *Pseudomonas aeruginosa*, which has been demonstrated efficacious against this bacterium in animal models.

The frequency of *Moraxella catarrhalis* infections has risen dramatically in the past few decades. This has been attributed to the emergence of multiply antibiotic resistant strains and an increasing population of people with weakened immune systems. It is no longer uncommon to isolate *Moraxella catarrhalis* strains that are resistant to some or all of the standard antibiotics. This phenomenon has created an unmet medical need and demand for new anti-microbial agents, vaccines, drug screening methods, and diagnostic tests for this organism.

SUMMARY OF THE INVENTION

The present invention relates to BASB081, in particular BASB081 polypeptides and BASB081 polynucleotides, recombinant materials and methods for their production. In another aspect, the invention relates to methods for using such polypeptides and polynucleotides, including prevention and treatment of microbial diseases, amongst others. In a further aspect, the invention relates to diagnostic assays for detecting diseases associated with microbial infections and conditions associated with such infections, such as assays for detecting expression or activity of BASB081 polynucleotides or polypeptides.

Various changes and modifications within the spirit and scope of the disclosed invention will become readily apparent to those skilled in the art from reading the following descriptions and from reading the other parts of the present disclosure.

BRIEF DESCRIPTION OF THE DRAWINGS

FIGS. 1A–1N show consecutive, aligned sequences for two BASB081 polynucleotides.

FIGS. 2A–2E show consecutive, aligned sequences for two BASB081 polypeptides.

DESCRIPTION OF THE INVENTION

Figure 3:
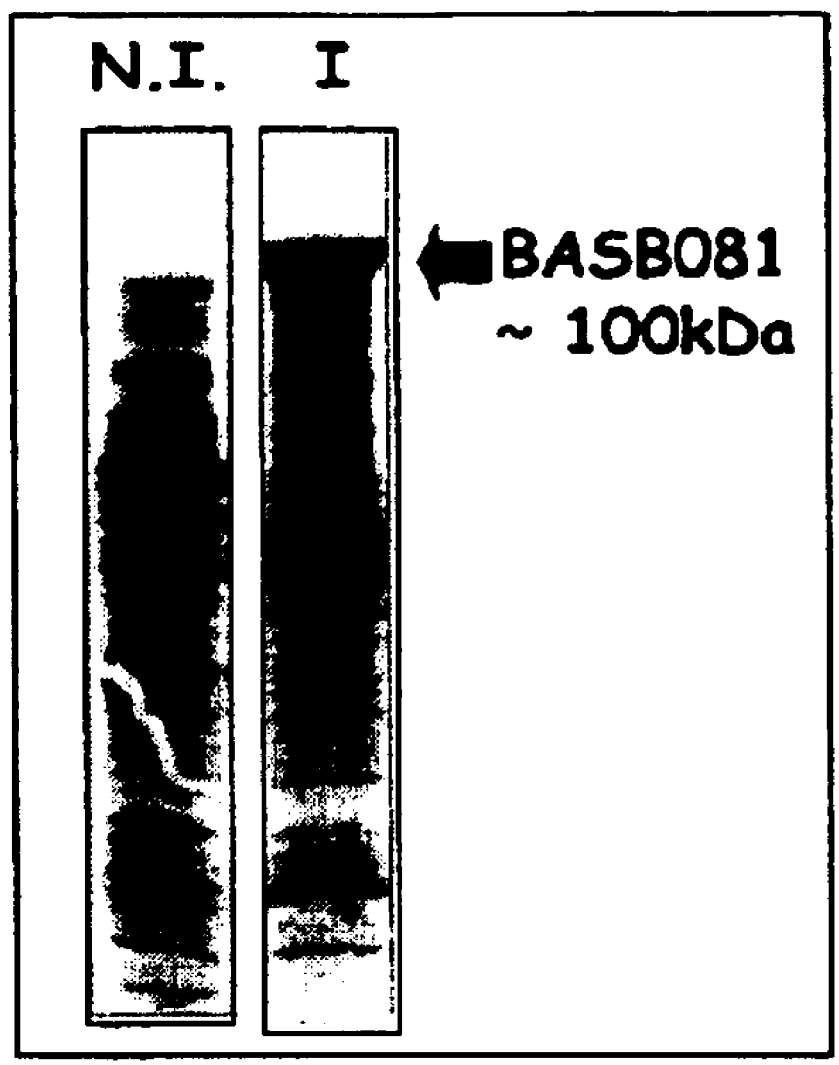
FIG. 3 shows an SDS-PAGE analysis of BASB081 expression in non induced (N.I.) or induced (I) *Escherichia coli* Top 10 cells.

The invention relates to BASB081 polypeptides and polynucleotides as described in greater detail below. In particular, the invention relates to polypeptides and polynucleotides of BASB081 of *Moraxella catarrhalis*, which is related by amino acid sequence homology to *Neisseria meningitidis* omp85 outer membrane protein. The invention relates especially to BASB081 having the nucleotide and amino acid sequences set out in SEQ ID NO:1 or 3 and SEQ ID NO:2 or 4 respectively. It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

Polypeptides

In one aspect of the invention there are provided polypeptides of *Moraxella catarrhalis* referred to herein as "BASB081" and "BASB081 potypeptides" as well as biologically, diagnostically, prophylactically, clinically or therapeutically useful variants thereof, and compositions comprising the same.

The present invention further provides for:

(a) an isolated polypeptide which comprises an amino acid sequence which has at least 85% identity, preferably at least 90% identity, more preferably at least 95% identity, most preferably at least 97–99% or exact identity, to that of SEQ ID NO:2 or 4;

(b) a polypeptide encoded by an isolated polynucleotide comprising a polynucleotide sequence which has at least 85% identity, preferably at least 90% identity, more preferably at least 95% identity, even more preferably at least 97–99% or exact identity to SEQ ID NO:1 or 3 over the entire length of SEQ ID NO:1 or 3 respectively; or (c) a polypeptide encoded by an isolated polynucleotide comprising a polynucleotide sequence encoding a polypeptide which has at least 85% identity, preferably at least 90% identity, more preferably at least 95% identity, even more preferably at least 97–99% or exact identity, to the amino acid sequence of SEQ ID NO:2 or 4.

The BASB081 polypeptides provided in SEQ ID NO:2 or 4 are the BASB081 polypeptides from *Moraxella catarrhalis* strain Mc2931 (ATCC 43617).

The invention also provides an immunogenic fragment of a BASB081 polypeptide, that is, a contiguous portion of the BASB081 polypeptide which has the same or substantially the same immunogenic activity as the polypeptide comprising the amino acid sequence of SEQ ID NO:2 or 4; That is to say, the fragment (if necessary when coupled to a carrier) is capable of raising an immune response which recognises the BASB081 polypeptide. Such an immunogenic fragment may include, for example, the BASB081 polypeptide lacking an N-terminal leader sequence, and/or a transmembrane domain and/or a C-terminal anchor domain. In a preferred aspect the immunogenic fragment of BASB081 according to the invention comprises substantially all of the extracellular domain of a polypeptide which has at least 85% identity, preferably at least 90% identity, more preferably at least 95% identity, most preferably at least 97–99% identity, to that of SEQ ID NO:2 or 4 over the entire length of SEQ ID NO:2

A fragment is a polypeptide having an amino acid sequence that is entirely the same as part but not all of any amino acid sequence of any polypeptide of the invention. As with BASB081 polypeptides, fragments may be "freestanding," or comprised within a larger polypeptide of which they form a part or region, most preferably as a single continuous region in a single larger polypeptide.

Preferred fragments include, for example, truncation polypeptides having a portion of an amino acid sequence of SEQ ID NO:2 or 4 or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2 or 4, or an isolated polypeptide comprising an amino acid sequence having at least 15, 20, 30, 40, 50 or 100 contiguous amino acids truncated or deleted from the amino acid sequence of SEQ ID NO:2 or 4.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5–10, 1–5, 1–3, 1–2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulins is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenzae virus, NS1 (hemagglutinin). Another fusion partner is the protein known as LytA. Preferably the C terminal portion of the molecule is used. Lyta is derived from *Streptococcus pneumoniae* which synthesize an N-acetyl-L-alanine amidase, amidase LytA, (coded by the lyta gene {Gene, 43 (1986) page 265–272}) an autolysin that specifically degrades certain bonds in the peptidoglycan backbone. The C-terminal domain of the LytA protein is responsible for the affinity to the choline or to some choline analogues such as DEAE. This property has been exploited for the development of *E.coli* C-LytA expressing plasmids useful for expression of fusion proteins. Purification of hybrid proteins containing the C-LytA fragment at its amino terminus has been described {Biotechnology: 10, (1992) page 795–798}. It is possible to use the repeat portion of the LytA molecule found in the C terminal end starting at residue 178, for example residues 188–305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from *Moraxella catarrhalis*, however, it may preferably be obtained from other organisms of the same taxonomic genus. A polypeptide of the invention may also be obtained, for example, from organisms of the same taxonomic family or order.

Polynucleotides

It is an object of the invention to provide polynucleotides that encode BASB081 polypeptides, particularly polynucleotides that encode the polypeptide herein designated BASB081.

In a particularly preferred embodiment of the invention the polynucleotide comprises a region encoding BASB081 polypeptides comprising a sequence set out in SEQ ID NO:1 or 3 which includes a full length gene, or a variant thereof.

The BASB081 polynucleotides provided in SEQ ID NO:1 or 3 are the BASB081 polynucleotides from *Moraxella catarrhalis* strain Mc2931 (ATCC 43617).

As a further aspect of the invention there are provided isolated nucleic acid molecules encoding and/or expressing BASB081 polypeptides and polynucleotides, particularly *Moraxella catarrhalis* BASB081 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB081 polypeptide having a deduced amino acid sequence of SEQ ID NO:2 or 4 and polynucleotides closely related thereto and variants thereof.

In another particularly preferred embodiment of the invention there is a BASB081 polypeptide from *Moraxella catarrhalis* comprising or consisting of an amino acid sequence of SEQ ID NO:2 or 4 or a variant thereof.

Using the information provided herein, such as a polynucleotide sequence set out in SEQ ID NO:1 or 3, a polynucleotide of the invention encoding BASB081 polypeptide may be obtained using standard cloning and screening methods, such as those for cloning and sequencing chromosomal DNA fragments from bacteria using *Moraxella catarrhalis* Catlin cells as starting material, followed by obtaining a full length clone. For example, to obtain a polynucleotide sequence of the invention, such as a polynucleotide sequence given in SEQ ID NO:1 or 3, typically a library of clones of chromosomal DNA of *Moraxella catarrhalis* Catlin in *E.coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:1 or 3 was discovered in a DNA library derived from *Moraxella catarrhalis*.

Moreover, each DNA sequence set out in SEQ ID NO:1 or 3 contains an open reading frame encoding a protein having about the number of amino acid residues set forth in SEQ ID NO:2 or 4 with a deduced molecular weight that can be calculated using amino acid residue molecular weight values well known to those skilled in the art.

The polynucleotide of SEQ ID NO:1, between the start codon at nucleotide number 1 and the stop codon which begins at nucleotide number 2758 of SEQ ID NO:1, encodes the polypeptide of SEQ ID NO:2.

The polynucleotide of SEQ ID NO:3, between the start codon at nucleotide number 1 and the stop codon which begins at nucleotide number 2668 of SEQ ID NO:3, encodes the polypeptide of SEQ ID NO:4.

In a further aspect, the present invention provides for an isolated polynucleotide comprising or consisting of:

(a) a polynucleotide sequence which has at least 85% identity, preferably at least 90% identity, more preferably at least 95% identity, even more preferably at least 97–99% or exact identity to SEQ ID NO:1 or 3 over the entire length of SEQ ID NO:1 or 3 respectively, or (b) a polynucleotide sequence encoding a polypeptide which has at least 85% identity, preferably at least 90% identity, more preferably at least 95% identity, even more preferably at least 97–99% or 100% exact, to the amino acid sequence of SEQ ID NO:2 or 4, over the entire length of SEQ ID NO:2 or 4 respectively.

A polynucleotide encoding a polypeptide of the present invention, including homologs and orthologs from species other than *Moraxella catarrhalis*, may be obtained by a process which comprises the steps of screening an appropriate library under stringent hybridization conditions (for example, using a temperature in the range of 45–65° C. and an SDS concentration from 0.1–1%) with a labeled or detectable probe consisting of or comprising the sequence of SEQ ID NO:1 or 3 or a fragment thereof; and isolating a full-length gene and/or genomic clones containing said polynucleotide sequence.

The invention provides a polynucleotide sequence identical over its entire length to a coding sequence (open reading frame) in SEQ ID NO:1 or 3. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB081 polypeptide of SEQ ID NO:2 or 4 may be identical to the polypeptide encoding sequence contained in nucleotides 1 to 2757 of SEQ ID NO:1 or the polypeptide encoding sequence contained in nucleotides 1 to 2667 of SEQ ID NO:3 respectively. Alternatively it may be a sequence, which as a result of the redundancy (degeneracy) of the genetic code, also encodes the polypeptide of SEQ ID NO:2 or 4.

The term "polynucleotide encoding a polypeptide" as used herein encompasses polynucleotides that include a sequence encoding a polypeptide of the invention, particularly a bacterial polypeptide and more particularly a polypeptide of the *Moraxella catarrhalis* BASB081 having an amino acid sequence set out in SEQ ID NO:2 or 4. The term also encompasses polynucleotides that include a single continuous region or discontinuous regions encoding the polypeptide (for example, polynucleotides interrupted by integrated phage, an integrated insertion sequence, an integrated vector sequence, an integrated tnansposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:2 or 4. Fragments of polynucleotides of the invention maybe used, for example, to synthesize full-length polynucleotides of the invention.

Further particularly preferred embodiments are polynucleotides encoding BASB081 variants, that have the amino acid sequence of BASB081 polypeptide of SEQ ID NO:2 or 4 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB081 polypeptide.

Further preferred embodiments of the invention are polynucleotides that are at least 85% identical over their entire length to a polynucleotide encoding BASB081 polypeptide having an amino acid sequence set out in SEQ ID NO:2 or 4, and polynucleotides that are complementary to such polynucleotides. Alternatively, most highly preferred are polynucleotides that comprise a region that is at least 90% identical over its entire length to a polynucleotide encoding BASB081 polypeptide and polynucleotides complementary thereto. In this regard, polynucleotides at least 95% identical over their entire length to the same are particularly preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:1 or 3.

In accordance with certain preferred embodiments of this invention there are provided polynucleotides that hybridize, particularly under stringent conditions, to BASB081 polynucleotide sequences, such as those polynucleotides in SEQ ID NO:1 or 3.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1 or 3 under stringent hybridization conditions with a probe having the sequence of said polynucleotide sequence set forth in SEQ ID NO:1 or 3 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB081 and to isolate cDNA and genomic clones of other genes that have a high identity, particularity high sequence identity, to the BASB081 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB081 gene may be isolated by screening using a DNA sequence provided in SEQ ID NO:1 or 3 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NO:1 or 3 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet* (1992) 1: 363, Manthorpe et al., *Hum. Gene Ther.* (1983) 4: 419), delivery of DNA complexed with specific protein carriers (Wu et al., *J Biol Chem.* (1989) 264: 16985), coprecipitation of DNA with calcium phosphate (Benvenisty & Reshef, *PNAS USA*, (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci, *E. coli*, streptomyces, cyanobacteria, *Bacillus subtilis*, *Neisseria meningitidis* and *Moraxella catarrhalis*; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picomaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc), Listeria, Salmonella, Shigella, BCG. These viruses and bacteria can be virulent, or attenuated in various ways in order to obtain live vaccines. Such live vaccines also form part of the invention.

Diagnostic, Prognostic, Serotyping and Mutation Assays

This invention is also related to the use of BASB081 polynucleotides and polypeptides of the invention for use as diagnostic reagents. Detection of BASB081 polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the BASB081 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled BASB081 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., Science, 230: 1242 (1985). Sequence changes at specific locations also may be revealed by nuclease protection assays, such as RNase, V1 and S1 protection assay or a chemical cleavage method. See, for example, Cotton et al., Proc. Natl. Acad. Sci., USA, 85: 4397–4401 (1985).

In another embodiment, an array of oligonucleotides probes comprising BASB081 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., Science, 274: 610 (1996)).

Thus in another aspect, the present invention relates to a diagnostic kit which comprises:

(a) a polynucleotide of the present invention, preferably the nucleotide sequence of SEQ ID NO:1 or 3, or a fragment thereof;

(b) a nucleotide sequence complementary to that of (a);

(c) a polypeptide of the present invention, preferably the polypeptide of SEQ ID NO:2 or 4 or a fragment thereof; or (d) an antibody to a polypeptide of the present invention, preferably to the polypeptide of SEQ ID NO:2 or 4.

It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferably SEQ ID NO:1 or 3, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding BASB081 polypeptide can be used to identify and analyze mutations.

The invention further provides primers with 1, 2, 3 or 4 nucleotides removed from the 5' and/or the 3' end. These primers may be used for, among other things, amplifying BASB081 DNA and/or RNA isolated from a sample derived from an individual, such as a bodily material. The primers maybe used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by Moraxella catarrhalis, comprising determining from a sample derived from an individual, such as a bodily material, an increased level of expression of polynucleotide having a sequence of SEQ ID NO:1 or 3. Increased or decreased expression of a BASB081 polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of BASB081 polypeptide compared to normal control tissue samples may be used to detect the presence of an infection, for example. Assay techniques that can be used to determine levels of a BASB081 polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probes obtained or derived from a bodily sample, to determine the presence of a particular polynucleotide sequence or related sequence in an individual. Such a presence may indicate the presence of a pathogen, particularly Moraxella catarrhalis, and may be useful in diagnosing and/or prognosing disease or a course of disease. A grid comprising a number of variants of the polynucleotide sequence of SEQ ID NO:1 or 3 are preferred. Also preferred is a comprising a number of variants of a polynucleotide sequence encoding the polypeptide sequence of SEQ ID NO:2 or 4.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against BASB081 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-BASB081 or from naive libraries (McCafferty, et al., (1990), Nature 348, 552–554; Marks, et al., (1992) *Biotechnology* 10, 779–783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against BASB081-polypeptide or BASB081-polynucleotide maybe employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarily determining region or regions of the hybridoma-derived antibody has been transplanted into a human monoclonal antibody, for example as described in Jones et al. (1986), *Nature* 321, 522–525 or Tempest et al., (1991) *Biotechnology* 9, 266–273.

Antagonists and Aponists-Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring BASB081 polypeptide and/or polynucleotide activity in the mixture, and comparing the BASB081 polypeptide and/or polynucleotide activity of the mixture to a standard. Fusion proteins, such as those made from Fc portion and BASB081 polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16) :9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of BASB081 polypeptides or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising BASB081 polypeptide and a labeled substrate or ligand of such polypeptide is incubated in the absence or the presence of a candidate molecule that may be a BASB081 agonist or antagonist. The ability of the candidate molecule to agonize or antagonize the BASB081 polypeptide is reflected in decreased binding of the labeled ligand or decreased production of product from such substrate. Molecules that bind gratuitously, i.e., without inducing the effects of BASB081 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in BASB081 polynucleotide or polypeptide activity, and binding assays known in the art.

Another example of an assay for BASB081 agonists is a competitive assay that combines BASB081 and a potential agonist with BASB081-binding molecules, recombinant BASB081 binding molecules, natural substrates or ligands, or substrate or ligand mimetics, under appropriate conditions for a competitive inhibition assay. BASB081 can be labeled, such as by radioactivity or a colorimetric compound, such that the number of BASB081 molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing BASB081-induced activities, thereby preventing the action or expression of BASB081 polypeptides and/or polynucleotides by excluding BASB081 polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, J. Neurochem. 56: 560 (1991); OLIGODEOXYNUCLEOTIDES AS ANTISENSE INHIBITORS OF GENE EXPRESSION, CRC Press, Boca Raton, Fla. (1988), for a description of these molecules). Preferred potential antagonists include compounds related to and variants of BASB081.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial BASB081 proteins that mediate tissue damage and/or; to block the normal progression of pathogenesis in infections initiated other than by the implantation of indwelling devices or by other surgical techniques.

In accordance with yet another aspect of the invention, there are provided BASB081 agonists and antagonists, preferably bacteristatic or bactericidal agonists and antagonists.

The antagonists and agonists of the invention maybe employed, for instance, to prevent, inhibit and/or treat diseases.

In a further aspect, the present invention relates to mimotopes of the polypeptide of the invention. A mimotopes is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with BASB081 polynucleotide and/or polypeptide, or a fragment or variant thereof, adequate to produce antibody and/or T cell immune response to protect said individual from infection, particularly bacterial infection and most particularly *Moraxella catarrhalis* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of BASB081 polynucleotide and/or polypeptide, or a fragment or a variant thereof, for expressing BASB081 polynucleotide and/or polypeptide, or a fragment or a variant thereof in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a BASB081 polynuclcotide and/or polypeptide encoded therefrom, wherein the composition comprises a recombinant BASB081 polynucleotide and/or polypeptide encoded therefrom and/or comprises DNA and/or RNA which encodes and expresses an antigen of said BASB081 polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

A BASB081 polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Haemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

Provided by this invention are compositions, particularly vaccine compositions, and methods comprising the polypeptides and/or polynucleotides of the invention and immunostimulatory DNA sequences, such as those described in Sato, Y. et al. Science 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *Moraxella catarrhalis*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Moraxella catarrhalis* infection, in mammals, particularly humans.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (Mosmann, T. R. and Coffman, R. L. (1989) TH1 and TH2 cells: *different patterns of lymphokine secretion lead to different functional properties. Annual Review of Immunology*, 7, p145–73). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL-4, IL5, IL-6 and IL-13.

It is known that certain vaccine adjuvants are particularly suited to the stimulation of either TH1 or TH2 -type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454).

3D-MPL will be present in the range of 10 μg–100 μg preferably 25–50 μg per dose wherein the antigen will typically be present in a range 2–50 μg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21: 3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 μg–200 μg, such as 10–100 μg, preferably 10 μg–50 μg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

While the invention has been described with reference to certain BASB081 polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

Compositions, Kits and Administration

In a further aspect of the invention there are provided compositions comprising a BASB081 polynucleotide and/or a BASB081 polypeptide for administration to a cell or to a multicellular organism.

The invention also relates to compositions comprising a polynucleotide and/or a polypeptides discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1–100 µg/kg of subject.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, cod usage analysis, nucleic acid base trimming, and sequencing chromatogram peak analysis.

A computer based method is provided for performing homology identification. This method comprises the steps of providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Definitions

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SLAM *J Applied Math*., 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J. Molec. Biol.* 215: 403–410 (1990), and FASTA(Pearson and Lipman Proc. Natl. Acad. Sci. USA 85; 2444–2448 (1988). The BLAST family of programs is publicly available from NCBI and other sources (BLAST *Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following:
Algorithm: Needleman and Wunsch, J. Mol Biol. 48: 443–453 (1970)
Comparison matrix: BLOSSUM62 from Henikoff and Henikoff,
Proc. Natl. Acad. Sci. USA. 89:10915–10919 (1992)
Gap Penalty: 8
Gap Length Penalty: 2
A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:
Algorithm: Needleman and Wunsch, J. Mol Biol. 48: 443–453 (1970)
Comparison matrix: matches=+10, mismatch=0
Gap Penalty 50
Gap Length Penalty: 3
Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it maybe 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or $$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, otitis media in infants and children, pneumonia in elderlies, sinusitis, nosocomial infections and invasive diseases, chronic otitis media with hearing loss, fluid accumulation in the middle ear, auditive nerve damage, delayed speech learning, infection of the upper respiratory tract and inflammation of the middle ear.

EXAMPLES

The examples below are carried out using standard techniques, which are well known and routine to those of skill in the art, except where otherwise described in detail. The examples are illustrative, but do not limit the invention.

Example 1

DNA Sequencing of the BASB081 Gene from *Moraxella Catarrhalis* Strain ATCC 43617.

A: BASB081 in *Moraxella Catarrhalis* Strain.

The BASB081 gene of SEQ ID NO:1 is from *Moraxella catarrhalis* strain ATCC 43617. The translation of the BASB081 polynucleotide sequence is showed in SEQ ID NO:2.

B: BASB081 in *Moraxella Catarrhalis* Strain 43617.

The sequence of the BASB081 gene was confirmed in *Moraxella Catarrhalis* strain ATCC 43617. For this purpose, plasmid DNA (see example 2A) containing the gene region encoding the mature BASB081 from *Morarelia Catarrhalis*. strain ATCC 43617 used as a PCR template. This material was then submitted to Polymerase Chain Reaction DNA amplification using primers *Moraxella catarrhalis* MCD15b-01 (5'-CAT GCC ATG GGT CAA CAA AAT AAC CCT GCA AAC-3') [SEQ ID NO:5] and reverse MCD15b-02 (5'CTA GTC TAG ATT AAA ATG GTG TGC CAA TAA AAA AAT G-3') [SEQ ID NO:6] specific for the BASB081 gene. The PCR amplicon was then submitted to DNA sequencing using the Big Dyes kit (Applied biosystems) and analyzed on a ABI 373/A DNA sequencer in the conditions described by the supplier. As a result, the polynucleotide and deduced polypeptide sequences, referred to as SEQ ID NO:3 and SEQ ID NO:4 respectively, were obtained. These sequences do not comprise the signal sequence as the signal sequence was from the plasmid.

Using the MegAlign program from the DNASTAR software package, an alignment of the polynucleotide sequences of SEQ ID NO:1 and 3 was performed, and is displayed in FIG. 1; a pairwise comparison of identities shows that the two BASB081 polynucleotide gene sequences are 99.9% identical in the region coding for the mature protein. Using the same MegAlign program, an alignment of the polypeptide sequences of SEQ ID NO:2 and 4 was performed, and is displayed in FIG. 2; a pairwise comparison of identities shows that the two BASB081 protein sequences are 99.9% identical in the region of the mature protein.

Example 2

Construction of Plasmid to Express Recombinant BASB081

A: Cloning of BASB081.

The NcoI and XbaI restriction sites (underlined) engineered into the primers *Moraxella catarrhalis* MCD15b-01 (5'-CAT GCC ATG GGT CAA CAA AAT AAC CCT GCA AAC-3') and reverse MCD15b-02 (5'CTA GTC TAG ATT AAA ATG GTG TGC CAA TAA AAA AAT G 3') amplification primers, respectively, permitted directional cloning of a BASB081 PCR product into the commercially available *E. coli* expression plasmid pBADgIII Calmodulin (Invitrogen, USA, ampicillin resistant). This plasmid provides the signal peptide from the bacteriophage fd pIII protein such that a mature BASB081 protein could be targeted to the periplasm of *E. coli*. The BASB081 PCR product was purified from the amplification reaction using Wizard PCR prep™ (Promega) according to the manufacturers instructions. To produce the required NcoI and XbaI termini necessary for cloning, purified PCR product was sequentially digested to completion with NcoI and XbaI restriction enzymes as recommended by the manufacturer (Boehringer Mannheim). Digested BASB081 PCR products and pBAD were gel-purified and ligated together using an approximately 5-fold molar excess of the digested fragment to the vector. A standard ~20 µl ligation reaction (~16° C., ~16 hours), using methods well known in the art, was performed using T4 DNA ligase (~2.0 units/reaction, Boehringer Mannheim). An aliquot of the ligation was used to transform electro-competent *E. coli* Top 10 cells according to methods well known in the art. Following a ~2–3 hour outgrowth period at 37° C. in ~1.0 ml of LB broth, transformed cells were plated on LB agar plates containing Ampicillin (50 µg/ml). Individual ampicillin-resistant colonies were selecteded and analyzed by whole cell-based PCR to verify that transformants contained the BASB081 DNA insert. Transformants that produced the expected PCR product were identified as strains containing a BASB081 expression construct. Expression plasmid containing strains were then analyzed for the inducible expression of recombinant BASB081.

B: Expression Analysis of PCR-Positive Transformants.

For each PCR-positive transformant identified above, ~5.0 ml of LB broth containing ampicillin (50 µg/ml) was inoculated with cells from the patch plate and grown overnight at 37° C. with shaking (~250 rpm). An aliquot of the overnight seed culture (~1.0 ml) was inoculated into a 125 ml erlenmeyer flask containing ~25 ml of LB ampicilline broth and grown at 37 ° C. with shaking (~250 rpm) until the culture turbidity reached O.D.600 of ~0.5, i.e. mid-log phase (usually about 1.5–2.0 hours). At this time approximately half of the culture (~12.5 ml) was transferred to a second 125 ml flask and expression of recombinant BASB081 protein induced by the addition of L-Arabinose to a final concentration of 0.2% (w/v). Incubation of both the arabinose-induced and non-induced cultures continued for an additional ~4 hours at 37 ° C. with shaking. Samples (~1.0 ml) of both induced and non-induced cultures were removed after the induction period and the cells collected by centrifugation in a microcentrifuge at room temperature for ~3 minutes. Individual cell pellets were suspended in ~50 µl of sterile water, then mixed with an equal volume of 2× Laemelli SDS-PAGE sample buffer containing 2-mercaptoethanol, and placed in boiling water bath for ~3 min to denature protein. Equal volumes (~15 µl) of both the crude arabinose-induced and the non-induced cell lysates were loaded onto duplicate 12% Tris/glycine polyacrylamide gel (1 mm thick Mini-gels, Novex). The induced and non-induced lysate samples were electrophoresed together with prestained molecular weight markers under conventional conditions using a standard SDS/Tris/glycine running buffer. Following electrophoresis, one gel was stained with commassie brilliant blue R250 (BioRad) and then destained to visualize novel BASB081 arabinose-inducible protein(s) (FIG. 3).

Deposited Materials

A deposit containing a *Moraxella catarrhalis* Catlin strain has been deposited with the American Type Culture Collection (herein "ATCC") on Jun. 21, 1997 and assigned deposit number 43617. The deposit was described as *Branhamella catarrhalis* (Frosch and Kolle) and is a freeze-dried, 1.5–2.9 kb insert library constructed from *M. catarrhalis* isolate obtained from a transtracheal aspirate of a coal miner with chronic bronchitits. The deposit is described in Antirnicrob. Agents Chemother. 21: 506–508 (1982).

The *Moraxella catarrhalis* strain deposit is referred to herein as "the deposited strain" or as "the DNA of the deposited strain."

The deposited strain contains a full length BASB081 gene.

A deposit of the vector pMC-D15 consisting of *Moraxella catarrhalis* DNA inserted in pQE30 has been deposited with the American Type Culture Collection (ATCC) on Feb. 12 1999 and assigned deposit number 207105.

The sequence of the polynucleotides contained in the deposited strain/clone, as well as the amino acid sequence of any polypeptide encoded thereby, are controlling in the event of any conflict with any description of sequences herein.

The deposit of the deposited strains have been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains are provided merely as convenience to those of skill in the art and are not an admission that a deposit is required for enablement, such as that required under 35 U.S.C. §112.

What is claimed is:

1. An isolated, recombinant polypeptide comprising a member selected from the group consisting of
   (a) the amino acid sequence SEQ ID NO:2;
   (b) an immunogenic fragment of at least contiguous 15 amino acids of SEQ ID NO:2;
wherein the immunogenic fragment, when administered to a subject in a suitable composition which can include an adjuvant, or a suitable carrier coupled to the polypeptide, induces an antibody or T-cell mediated immune response that recognizes the polypeptide SEQ ID NO:2.

2. The isolated, recombinant polypeptide of claim 1, wherein the polypeptide is according to (a).

3. The isolated, recombinant polypeptide of claim 1, wherein the polypeptide is according to (b).

4. The isolated, recombinant polypeptide of claim 1, wherein the immunogenic fragment of (b) comprises at least 20 contiguous amino acids of SEQ ID NO:2, wherein the isolated polypeptide, when administered to a subject in a suitable composition which can include an adjuvant, or a suitable carrier coupled to the polypeptide, induces an antibody or T-cell mediated immune response that recognizes the polypeptide SEQ ID NO:2.

5. The isolated, recombinant polypeptide of claim 1 wherein the isolated, recombinant polypeptide of (a) consists of SEQ ID NO:2.

6. A fusion protein comprising the isolated, recombinant polypeptide of claim 1.

7. An immunogenic composition comprising the isolated, recombinant polypeptide of claim 1 and a pharmaceutically acceptable carrier.

8. The immunogenic composition of claim 7, wherein the immunogenic composition comprises at least one other *Moraxella catarrhalis* antigen in addition to the antigen provided by the isolated recombinant polypeptide.

9. A method for inducing an immune response in a mammal comprising administration of the isolated, recombinant polypeptide of claim 1.

10. A fusion protein comprising the isolated, recombinant polypeptide of claim 2.

11. A fusion protein comprising the isolated, recombinant polypeptide of claim 3.

12. An immunogenic composition comprising the isolated, recombinant polypeptide of claim 2.

13. An immunogenic composition comprising the isolated, recombinant polypeptide of claim 3.

14. An isolated polypeptide consisting of SEQ ID NO:2.

* * * * *

SEQUENCE LISTING

```
<160> NUMBER OF SEQ ID NOS: 6

<210> SEQ ID NO 1
<211> LENGTH: 2760
<212> TYPE: DNA
<213> ORGANISM: Moraxella catarrhalis

<400> SEQUENCE: 1
atgtcaaagc ccgttttgtt tgcaaatcgc agttttatgc ctgtcgcatt ggcggcttat      60
ttgcctttga tgacatcgca agcattggca caacaaaata accctgcaaa catcatcaat     120
catgtacccg ctcatgacac cgccatcaat caagcaaagg caggcaatcc gcctgttttg     180
```

-continued

| | | | | | |
|---|---|---|---|---|---|
| ctaacacctg | agcagataca | agcacgcctt | aatgctgctg | gactgaatgc | taagccccaa | 240 |
| tcacaagctt | tggatgttgt | caattttgat | gatcaatcgc | cgatatctcg | tatcggtgag | 300 |
| caatcacccc | ctttgggttt | ggatatgtcg | gtcatcgaag | aaaccacacc | gctaagcttg | 360 |
| gaggaattat | ttgctcaaga | atctactgag | atgggaatca | atccaaatga | ttatattcca | 420 |
| gaatatcaag | gcgagcaacc | taatagtgag | gtggttgtac | caccgacatt | agaacctgaa | 480 |
| aaaccaggtt | tgatcaagcg | tctttatgca | cgcctattta | atgatggtgt | caataaggtg | 540 |
| cctaggctta | aggcaaaatt | ttatcaatca | tcgcaatcag | gcgaaaccag | tgcgattggg | 600 |
| tcatcgcatc | aaaaaacaga | gccttatgca | aatatcaaag | cagcacttga | agacatcacc | 660 |
| caagagtcag | cgatggattt | gaatggctct | atcccacgcc | taaggcaaac | tgctttggtg | 720 |
| gcagcgcgtg | ctgtcggtta | ttatgatatt | gatttatcaa | tcataagaaa | tagcatcgga | 780 |
| gaggtggatg | tcatcatcca | tgatttaggt | gaacctgttt | atattgatta | tcgagcggtg | 840 |
| gaggtacgag | gtgaaggtgc | tgatgataaa | gcatttacta | ccgtggcgga | tgaggtgcca | 900 |
| ttgctgatcg | gcgatgtctt | tcatcatggc | aagtacgaaa | ccaaaaaaaa | tctcatcgaa | 960 |
| aatgccagtg | ctgaacatgg | atattttgat | gggcgttggc | tggatcgttc | agttgatgta | 1020 |
| attttgccag | ataataccgc | tgatgtcagc | ttaatttatg | atacaggtac | gcagtatcgc | 1080 |
| tttgatgagg | tggtattttt | taccattgat | cctaaaacca | atcaattgac | aaccgatcca | 1140 |
| gataagctgc | cagttaaacg | agaattactt | gagcagttac | tcaccgttaa | catgggagag | 1200 |
| gcttacaatt | tacaggcggt | gcgtgcactt | tcaaatgatt | tgattgccac | acggtatttt | 1260 |
| aatatggtga | ataccgagat | tgtctttcca | gagcgtgaac | agatccaaaa | cgaccaagtg | 1320 |
| agctttgagc | agtcttcaag | tagccgtact | gaaccagcac | aagttgatga | aagcacactt | 1380 |
| gaacctgtca | ttgaaaccgt | tgagctaacg | gatgggatat | taatggatat | ttcgcccatc | 1440 |
| gaatttagtg | catctaatct | gattcaagac | aagctaaatt | tggtggctgc | caaggctcgc | 1500 |
| catttatatg | acatgcctga | tgataggtg | cttgccatca | atcatgatga | tggcgtaaat | 1560 |
| cgctctatttt | tgggcagaat | cagcgatgcc | gtatctgccg | ttgcacgtgc | tatttttacct | 1620 |
| gatgaatctg | aaaatgaggt | aatagatttg | cccgagcgta | ccgcattggc | taatcgcaag | 1680 |
| accccctgctg | atgtctatca | aagtaaaaaa | gtgccgctat | atgtctttgt | ggcgagtgat | 1740 |
| aaaccacgag | atggtcaaat | tggtttgggc | tggggatcgg | acacaggtac | ccgcctagtc | 1800 |
| acaaaatttg | agcataattt | gattaatcgt | gatggctatc | aagcaggcgc | tgagctaaga | 1860 |
| ctgtctgagg | ataaaaaagg | ggtcaagtta | tatgccacca | aaccgcttag | ccaccctcta | 1920 |
| aatgatcagc | taagagcaac | tttgggttat | caacaagaag | tttttggtca | ctctaccaat | 1980 |
| ggttttgatt | tatccacacg | caccctagag | catgagatta | gccgcagtat | tatccaaaat | 2040 |
| ggtggctgga | atcgtactta | ttcattgcgt | tatcgtcttg | ataagcttaa | aacccaagca | 2100 |
| cccccctgaaa | catggcagga | tttaccagtg | gattttgtca | atggtaagcc | aagccaagag | 2160 |
| gcgttattgg | caggtgttgc | tgtgcataaa | acggttgcag | ataatttggt | taatccgatg | 2220 |
| cgtggctatc | gtcagcgata | ttctttagag | gttggctcaa | gcggtttggt | atcggatgct | 2280 |
| aatatgcta | ttgctcgagc | tggtattagt | ggcgtgtata | gttttgggga | taatgcttat | 2340 |
| ggcagcaatc | gtgcccatca | gatgactggt | ggcatacaag | caggatacat | ttggtcggat | 2400 |
| aatttttaatc | atgtgccata | tcgtttgcgt | ttttttgctg | gtggcgacca | aagtattcgt | 2460 |
| ggatatgcac | atgacagttt | atcacctata | tcagataagg | gttatctgac | aggcggtcaa | 2520 |

-continued

```
gtattggcgg ttggtacagc tgaatataat tatgaattta tgaaagattt gcgtttggcg      2580
gtttttggtg atattggtaa tgcttatgat aaaggcttta ctaatgatac caaaattggt      2640
gcaggtgtcg gtgttcgctg ggcatcacct gtcggtcaag ttcgtgttga tgtggcaact      2700
ggtgtcaaag aagagggcaa tcccattaag ctgcattttt ttattggcac accatttta     2760
```

<210> SEQ ID NO 2
<211> LENGTH: 919
<212> TYPE: PRT
<213> ORGANISM: Moraxella catarrhalis

<400> SEQUENCE: 2

```
Met Ser Lys Pro Val Leu Phe Ala Asn Arg Ser Phe Met Pro Val Ala
 1               5                  10                  15

Leu Ala Ala Tyr Leu Pro Leu Met Thr Ser Gln Ala Leu Ala Gln Gln
                20                  25                  30

Asn Asn Pro Ala Asn Ile Ile Asn His Val Pro Ala His Asp Thr Ala
            35                  40                  45

Ile Asn Gln Ala Lys Ala Gly Asn Pro Pro Val Leu Leu Thr Pro Glu
        50                  55                  60

Gln Ile Gln Ala Arg Leu Asn Ala Ala Gly Leu Asn Ala Lys Pro Gln
 65                  70                  75                  80

Ser Gln Ala Leu Asp Val Val Asn Phe Asp Asp Gln Ser Pro Ile Ser
                85                  90                  95

Arg Ile Gly Glu Gln Ser Pro Pro Leu Gly Leu Asp Met Ser Val Ile
            100                 105                 110

Glu Glu Thr Thr Pro Leu Ser Leu Glu Glu Leu Phe Ala Gln Glu Ser
        115                 120                 125

Thr Glu Met Gly Ile Asn Pro Asn Asp Tyr Ile Pro Glu Tyr Gln Gly
    130                 135                 140

Glu Gln Pro Asn Ser Glu Val Val Pro Pro Thr Leu Glu Pro Glu
145                 150                 155                 160

Lys Pro Gly Leu Ile Lys Arg Leu Tyr Ala Arg Leu Phe Asn Asp Gly
                165                 170                 175

Val Asn Lys Val Pro Arg Leu Lys Ala Lys Phe Tyr Gln Ser Ser Gln
            180                 185                 190

Ser Gly Glu Thr Ser Ala Ile Gly Ser Ser His Gln Lys Thr Glu Pro
        195                 200                 205

Tyr Ala Asn Ile Lys Ala Ala Leu Glu Asp Ile Thr Gln Glu Ser Ala
    210                 215                 220

Met Asp Leu Asn Gly Ser Ile Pro Arg Leu Arg Gln Thr Ala Leu Val
225                 230                 235                 240

Ala Ala Arg Ala Val Gly Tyr Tyr Asp Ile Asp Leu Ser Ile Ile Arg
                245                 250                 255

Asn Ser Ile Gly Glu Val Asp Val Ile His Asp Leu Gly Glu Pro
            260                 265                 270

Val Tyr Ile Asp Tyr Arg Ala Val Glu Val Arg Gly Glu Gly Ala Asp
        275                 280                 285

Asp Lys Ala Phe Thr Thr Val Ala Asp Glu Val Pro Leu Leu Ile Gly
    290                 295                 300

Asp Val Phe His His Gly Lys Tyr Glu Thr Lys Lys Asn Leu Ile Glu
305                 310                 315                 320

Asn Ala Ser Ala Glu His Gly Tyr Phe Asp Gly Arg Trp Leu Asp Arg
                325                 330                 335
```

-continued

```
Ser Val Asp Val Ile Leu Pro Asp Asn Thr Ala Asp Val Ser Leu Ile
            340                 345                 350
Tyr Asp Thr Gly Thr Gln Tyr Arg Phe Asp Glu Val Phe Phe Thr
            355                 360                 365
Ile Asp Pro Lys Thr Asn Gln Leu Thr Thr Asp Pro Asp Lys Leu Pro
            370                 375                 380
Val Lys Arg Glu Leu Leu Glu Gln Leu Leu Thr Val Asn Met Gly Glu
385                 390                 395                 400
Ala Tyr Asn Leu Gln Ala Val Arg Ala Leu Ser Asn Asp Leu Ile Ala
                405                 410                 415
Thr Arg Tyr Phe Asn Met Val Asn Thr Glu Ile Val Phe Pro Glu Arg
                420                 425                 430
Glu Gln Ile Gln Asn Asp Gln Val Ser Phe Glu Gln Ser Ser Ser Ser
                435                 440                 445
Arg Thr Glu Pro Ala Gln Val Asp Glu Ser Thr Leu Glu Pro Val Ile
            450                 455                 460
Glu Thr Val Glu Leu Thr Asp Gly Ile Leu Met Asp Ile Ser Pro Ile
465                 470                 475                 480
Glu Phe Ser Ala Ser Asn Leu Ile Gln Asp Lys Leu Asn Leu Val Ala
                485                 490                 495
Ala Lys Ala Arg His Leu Tyr Asp Met Pro Asp Asp Arg Val Leu Ala
            500                 505                 510
Ile Asn His Asp Asp Gly Val Asn Arg Ser Ile Leu Gly Arg Ile Ser
            515                 520                 525
Asp Ala Val Ser Ala Val Ala Arg Ala Ile Leu Pro Asp Glu Ser Glu
            530                 535                 540
Asn Glu Val Ile Asp Leu Pro Glu Arg Thr Ala Leu Ala Asn Arg Lys
545                 550                 555                 560
Thr Pro Ala Asp Val Tyr Gln Ser Lys Lys Val Pro Leu Tyr Val Phe
                565                 570                 575
Val Ala Ser Asp Lys Pro Arg Asp Gly Gln Ile Gly Leu Gly Trp Gly
            580                 585                 590
Ser Asp Thr Gly Thr Arg Leu Val Thr Lys Phe Glu His Asn Leu Ile
            595                 600                 605
Asn Arg Asp Gly Tyr Gln Ala Gly Ala Glu Leu Arg Leu Ser Glu Asp
            610                 615                 620
Lys Lys Gly Val Lys Leu Tyr Ala Thr Lys Pro Leu Ser His Pro Leu
625                 630                 635                 640
Asn Asp Gln Leu Arg Ala Thr Leu Gly Tyr Gln Gln Glu Val Phe Gly
                645                 650                 655
His Ser Thr Asn Gly Phe Asp Leu Ser Thr Arg Thr Leu Glu His Glu
            660                 665                 670
Ile Ser Arg Ser Ile Ile Gln Asn Gly Gly Trp Asn Arg Thr Tyr Ser
            675                 680                 685
Leu Arg Tyr Arg Leu Asp Lys Leu Lys Thr Gln Ala Pro Pro Glu Thr
            690                 695                 700
Trp Gln Asp Leu Pro Val Asp Phe Val Asn Gly Lys Pro Ser Gln Glu
705                 710                 715                 720
Ala Leu Leu Ala Gly Val Ala Val His Lys Thr Val Ala Asp Asn Leu
                725                 730                 735
Val Asn Pro Met Arg Gly Tyr Arg Gln Arg Tyr Ser Leu Glu Val Gly
                740                 745                 750
Ser Ser Gly Leu Val Ser Asp Ala Asn Met Ala Ile Ala Arg Ala Gly
```

```
              755                 760                 765
Ile Ser Gly Val Tyr Ser Phe Gly Asp Asn Ala Tyr Gly Ser Asn Arg
        770                 775                 780

Ala His Gln Met Thr Gly Gly Ile Gln Ala Gly Tyr Ile Trp Ser Asp
785                 790                 795                 800

Asn Phe Asn His Val Pro Tyr Arg Leu Arg Phe Ala Gly Gly Asp
                805                 810                 815

Gln Ser Ile Arg Gly Tyr Ala His Asp Ser Leu Ser Pro Ile Ser Asp
            820                 825                 830

Lys Gly Tyr Leu Thr Gly Gly Gln Val Leu Ala Val Gly Thr Ala Glu
            835                 840                 845

Tyr Asn Tyr Glu Phe Met Lys Asp Leu Arg Leu Ala Val Phe Gly Asp
850                 855                 860

Ile Gly Asn Ala Tyr Asp Lys Gly Phe Thr Asn Asp Thr Lys Ile Gly
865                 870                 875                 880

Ala Gly Val Gly Val Arg Trp Ala Ser Pro Val Gly Gln Val Arg Val
                885                 890                 895

Asp Val Ala Thr Gly Val Lys Glu Glu Gly Asn Pro Ile Lys Leu His
            900                 905                 910

Phe Phe Ile Gly Thr Pro Phe
        915
```

<210> SEQ ID NO 3
<211> LENGTH: 2670
<212> TYPE: DNA
<213> ORGANISM: Moraxella catarrhalis

<400> SEQUENCE: 3

```
caacaaaata accctgcaaa catcatcaat catgtacccg ctcatgacac cgccatcaat     60
caagcaaagg caggcaatcc gcctgttttg ctaacacctg agcagataca agcacgcctt    120
aatgctgctg gactgaatgc taagccccaa tcacaagctt tggatgttgt caattttgat    180
gatcaatcgc cgatatctcg tatcggtgag caatcacccc cttggggttt ggatatgtcg    240
gtcatcgaag aaaccacacc gctaagcttg gaggaattat ttgctcaaga atctactgag    300
atgggaatca atccaaatga ttatattcca gaatatcaag gcgagcaacc taatagtgag    360
gtggttgtac caccgacatt agaacctgaa aaaccaggtt tgatcaagcg tctttatgca    420
cgcctattta atgatggtgt caataaggtg cctaggctta aggcaaaatt ttatcaatca    480
tcgcaatcag gcgaaaccag tgcgattggg tcatcgcatc aaaaaacaga gccttatgca    540
aatatcaaag cagcacttga agacatcacc caagagtcag cgatggattt gaatggctct    600
atcccacgcc taaggcaaac tgctttggtg gcagcgcgtg ctgtcggtta ttatgatatt    660
gatttatcaa tcataagaaa tagcatcgga gaggtggatg tcatcatcca tgatttaggt    720
gaacctgttt atattgatta tcgagcggtg gaggtacgag gtgaaggtgc tgatgataaa    780
gcatttacta ccgtggcgga tgaggtgcca ttgctgatcg gcgatgtctt tcatcacggc    840
aagtacgaaa ccaaaaaaaa tctcatcgaa aatgccagtg ctgaacatgg atattttgat    900
gggcgttggc tggatcgttc agttgatgta attttgccag ataataccgc tgatgtcagc    960
ttaatttatg atacaggtac gcagtatcgc tttgatgagg tgatatttt taccattgat   1020 cctaaaacca atcaattgac aaccgatcca gataagctgc cagttaaacg agaattactt   1080
gagcagttac tcaccgttaa catgggagag gcttacaatt tacaggcggt gcgtgcactt   1140
tcaaatgatt tgattgccac acggtatttt aatatggtga ataccgagat tgtctttcca   1200
```

-continued

```
gagcgtgaac agatccaaaa cgaccaagtg agctttgagc agtcttcaag tagccgtact    1260
gaaccagcac aagttgatga agcacactt  gaacctgtca ttgaaaccgt tgagctaacg    1320
gatgggatat taatgatat  ttcgcccatc gaatttagtg catctaatct gattcaagac    1380
aagctaaatt tggtggctgc caaggctcgc catttatatg acatgcctga tgatagggtg    1440
cttgccatca atcatgatga tggcgtaaat cgctctattt tgggcagaat cagcgatgcc    1500
gtatctgccg ttgcacgtgc tatttacct  gatgaatctg aaaatgaggt aatagatttg    1560
cccgagcgta ccgcattggc taatcgcaag acccctgctg atgtctatca agtaaaaaaa    1620
gtgccgctat atgtctttgt ggcgagtgat aaaccccgag atggtcaaat tggtttgggc    1680
tggggatcgg acacaggtac ccgcctagtc acaaaatttg agcataattt gattaatcgt    1740
gatggctatc aagcaggcgc tgagctaaga ctgtctgagg ataaaaaagg ggtcaagtta    1800
tatgccacca aaccgcttag ccaccctcta aatgatcagc taagagcaac tttgggttat    1860
caacaagaag ttttttggtca ctctaccaat ggttttgatt tatccacacg caccctagag    1920
catgagatta gccgcagtat tatccaaaat ggtggctgga atcgtactta ttcattgcgt    1980
tatcgtcttg ataagcttaa aacccaagca ccccctgaaa catggcagga tttaccagtg    2040
gattttgtca atggtaagcc aagccaagag gcgttattgg caggtgttgc tgtgcataaa    2100
acggttgcag ataatttggt taatccgatg cgtggctatc gtcagcgata ttctttagag    2160
gttggctcaa gcggtttggt atcggatgct aatatggcta ttgctcgagc tggtattagt    2220
ggcgtgtata gttttgggga taatgcttat ggcagcaatc gtgcccatca gatgactggt    2280
ggcatacaag caggatacat ttggtcggat aattttaatc atgtgccata tcgtttgcgt    2340 tttttttgctg gtgtgcgacca aagtattcgt ggatatgcac atgacagttt atcacctata    2400
tcagataagg gttatctgac aggcggtcaa gtattggcgg ttggtacagc tgaatataat    2460
tatgaattta tgaaagattt gcgtttggcg gttttttggtg atattggtaa tgcttatgat    2520
aaaggcttta ctaatgatac caaaattggt gcaggtgtcg gtgttcgctg gcatcaccct    2580
gtcggtcaag ttcgtgttga tgtggcaact ggtgtcaaag aagagggcaa tcccattaag    2640
ctgcattttt ttattggcac accatttaa                                       2670
```

<210> SEQ ID NO 4
<211> LENGTH: 889
<212> TYPE: PRT
<213> ORGANISM: Moraxella catarrhalis

<400> SEQUENCE: 4

```
Gln Gln Asn Asn Pro Ala Asn Ile Ile Asn His Val Pro Ala His Asp
  1               5                  10                  15

Thr Ala Ile Asn Gln Ala Lys Ala Gly Asn Pro Pro Val Leu Leu Thr
             20                  25                  30

Pro Glu Gln Ile Gln Ala Arg Leu Asn Ala Ala Gly Leu Asn Ala Lys
         35                  40                  45

Pro Gln Ser Gln Ala Leu Asp Val Val Asn Phe Asp Asp Gln Ser Pro
     50                  55                  60

Ile Ser Arg Ile Gly Glu Gln Ser Pro Pro Leu Gly Leu Asp Met Ser
 65                  70                  75                  80

Val Ile Glu Glu Thr Thr Pro Leu Ser Leu Glu Glu Leu Phe Ala Gln
                 85                  90                  95

Glu Ser Thr Glu Met Gly Ile Asn Pro Asn Asp Tyr Ile Pro Glu Tyr
            100                 105                 110
```

```
Gln Gly Glu Gln Pro Asn Ser Glu Val Val Pro Pro Thr Leu Glu
            115                 120                 125
Pro Glu Lys Pro Gly Leu Ile Lys Arg Leu Tyr Ala Arg Leu Phe Asn
        130                 135                 140
Asp Gly Val Asn Lys Val Pro Arg Leu Lys Ala Lys Phe Tyr Gln Ser
145                 150                 155                 160
Ser Gln Ser Gly Glu Thr Ser Ala Ile Gly Ser Ser His Gln Lys Thr
                165                 170                 175
Glu Pro Tyr Ala Asn Ile Lys Ala Ala Leu Glu Asp Ile Thr Gln Glu
            180                 185                 190
Ser Ala Met Asp Leu Asn Gly Ser Ile Pro Arg Leu Arg Gln Thr Ala
        195                 200                 205
Leu Val Ala Ala Arg Ala Val Gly Tyr Tyr Asp Ile Asp Leu Ser Ile
    210                 215                 220
Ile Arg Asn Ser Ile Gly Glu Val Asp Val Ile His Asp Leu Gly
225                 230                 235                 240
Glu Pro Val Tyr Ile Asp Tyr Arg Ala Val Glu Val Arg Gly Glu Gly
            245                 250                 255
Ala Asp Asp Lys Ala Phe Thr Thr Val Ala Asp Glu Val Pro Leu Leu
        260                 265                 270
Ile Gly Asp Val Phe His His Gly Lys Tyr Glu Thr Lys Lys Asn Leu
    275                 280                 285
Ile Glu Asn Ala Ser Ala Glu His Gly Tyr Phe Asp Gly Arg Trp Leu
    290                 295                 300
Asp Arg Ser Val Asp Val Ile Leu Pro Asp Asn Thr Ala Asp Val Ser
305                 310                 315                 320
Leu Ile Tyr Asp Thr Gly Thr Gln Tyr Arg Phe Asp Glu Val Ile Phe
            325                 330                 335
Phe Thr Ile Asp Pro Lys Thr Asn Gln Leu Thr Thr Asp Pro Asp Lys
        340                 345                 350
Leu Pro Val Lys Arg Glu Leu Leu Glu Gln Leu Leu Thr Val Asn Met
    355                 360                 365
Gly Glu Ala Tyr Asn Leu Gln Ala Val Arg Ala Leu Ser Asn Asp Leu
    370                 375                 380
Ile Ala Thr Arg Tyr Phe Asn Met Val Asn Thr Glu Ile Val Phe Pro
385                 390                 395                 400
Glu Arg Glu Gln Ile Gln Asn Asp Gln Val Ser Phe Glu Gln Ser Ser
            405                 410                 415
Ser Ser Arg Thr Glu Pro Ala Gln Val Asp Glu Ser Thr Leu Glu Pro
        420                 425                 430
Val Ile Glu Thr Val Glu Leu Thr Asp Gly Ile Leu Met Asp Ile Ser
    435                 440                 445
Pro Ile Glu Phe Ser Ala Ser Asn Leu Ile Gln Asp Lys Leu Asn Leu
    450                 455                 460
Val Ala Ala Lys Ala Arg His Leu Tyr Asp Met Pro Asp Asp Arg Val
465                 470                 475                 480
Leu Ala Ile Asn His Asp Gly Val Asn Arg Ser Ile Leu Gly Arg
            485                 490                 495
Ile Ser Asp Ala Val Ser Ala Val Ala Arg Ala Ile Leu Pro Asp Glu
        500                 505                 510
Ser Glu Asn Glu Val Ile Asp Leu Pro Glu Arg Thr Ala Leu Ala Asn
    515                 520                 525
```

-continued

```
Arg Lys Thr Pro Ala Asp Val Tyr Gln Ser Lys Lys Val Pro Leu Tyr
            530                 535                 540
Val Phe Val Ala Ser Asp Lys Pro Arg Asp Gly Gln Ile Gly Leu Gly
545                 550                 555                 560
Trp Gly Ser Asp Thr Gly Thr Arg Leu Val Thr Lys Phe Glu His Asn
                565                 570                 575
Leu Ile Asn Arg Asp Gly Tyr Gln Ala Gly Ala Glu Leu Arg Leu Ser
            580                 585                 590
Glu Asp Lys Lys Gly Val Lys Leu Tyr Ala Thr Lys Pro Leu Ser His
            595                 600                 605
Pro Leu Asn Asp Gln Leu Arg Ala Thr Leu Gly Tyr Gln Gln Glu Val
610                 615                 620
Phe Gly His Ser Thr Asn Gly Phe Asp Leu Ser Thr Arg Thr Leu Glu
625                 630                 635                 640
His Glu Ile Ser Arg Ser Ile Ile Gln Asn Gly Gly Trp Asn Arg Thr
                645                 650                 655
Tyr Ser Leu Arg Tyr Arg Leu Asp Lys Leu Lys Thr Gln Ala Pro Pro
            660                 665                 670
Glu Thr Trp Gln Asp Leu Pro Val Asp Phe Val Asn Gly Lys Pro Ser
            675                 680                 685
Gln Glu Ala Leu Leu Ala Gly Val Ala Val His Lys Thr Val Ala Asp
690                 695                 700
Asn Leu Val Asn Pro Met Arg Gly Tyr Arg Gln Arg Tyr Ser Leu Glu
705                 710                 715                 720
Val Gly Ser Ser Gly Leu Val Ser Asp Ala Asn Met Ala Ile Ala Arg
                725                 730                 735
Ala Gly Ile Ser Gly Val Tyr Ser Phe Gly Asp Asn Ala Tyr Gly Ser
            740                 745                 750
Asn Arg Ala His Gln Met Thr Gly Gly Ile Gln Ala Gly Tyr Ile Trp
            755                 760                 765
Ser Asp Asn Phe Asn His Val Pro Tyr Arg Leu Arg Phe Phe Ala Gly
770                 775                 780
Gly Asp Gln Ser Ile Arg Gly Tyr Ala His Asp Ser Leu Ser Pro Ile
785                 790                 795                 800
Ser Asp Lys Gly Tyr Leu Thr Gly Gly Gln Val Leu Ala Val Gly Thr
                805                 810                 815
Ala Glu Tyr Asn Tyr Glu Phe Met Lys Asp Leu Arg Leu Ala Val Phe
            820                 825                 830
Gly Asp Ile Gly Asn Ala Tyr Asp Lys Gly Phe Thr Asn Asp Thr Lys
            835                 840                 845
Ile Gly Ala Gly Val Gly Val Arg Trp Ala Ser Pro Val Gly Gln Val
850                 855                 860
Arg Val Asp Val Ala Thr Gly Val Lys Glu Glu Gly Asn Pro Ile Lys
865                 870                 875                 880
Leu His Phe Phe Ile Gly Thr Pro Phe
                885
```

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5

```
catgccatgg gtcaacaaaa taaccctgca aac                          33
```

<210> SEQ ID NO 6
<211> LENGTH: 37
<212> TYPE: DNA
<213> ORGANISM: Artificial Sequence
<220> FEATURE:
<223> OTHER INFORMATION: Primer

<400> SEQUENCE: 6

```
ctagtctaga ttaaaatggt gtgccaataa aaaaatg                      37
```